United States Patent
Kutyavin et al.

(10) Patent No.: US 11,819,584 B2
(45) Date of Patent: Nov. 21, 2023

(54) NUCLEIC ACID DECONTAMINATION METHODS

(71) Applicant: Cepheid, Sunnyvale, CA (US)

(72) Inventors: Alex I. Kutyavin, Sunnyvale, CA (US); Kevin P. Lund, Sunnyvale, CA (US); Oliver Z. Nanassy, Sunnyvale, CA (US); Alexander A. Gall, Sunnyvale, CA (US); William Brabant, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 306 days.

(21) Appl. No.: 17/269,230

(22) PCT Filed: Aug. 16, 2019

(86) PCT No.: PCT/US2019/046925
§ 371 (c)(1),
(2) Date: Feb. 17, 2021

(87) PCT Pub. No.: WO2020/037270
PCT Pub. Date: Feb. 20, 2020

(65) Prior Publication Data
US 2021/0162085 A1    Jun. 3, 2021

Related U.S. Application Data

(60) Provisional application No. 62/765,014, filed on Aug. 17, 2018.

(51) Int. Cl.
*A61L 2/18* (2006.01)
*A61L 2/00* (2006.01)
(Continued)

(52) U.S. Cl.
CPC ............... *A61L 2/18* (2013.01); *A61L 2/0005* (2013.01); *A61L 9/013* (2013.01); *A61L 9/145* (2013.01);
(Continued)

(58) Field of Classification Search
CPC ........ A61L 2/18; A61L 2209/21; A61L 9/013; A61L 2/0005
See application file for complete search history.

(56) References Cited

U.S. PATENT DOCUMENTS

| | | | |
|---|---|---|---|
| 5,384,400 A | 1/1995 | Crescenzi et al. | |
| 5,763,186 A | 6/1998 | Ludtke et al. | |

(Continued)

FOREIGN PATENT DOCUMENTS

| | | |
|---|---|---|
| AU | 2002306077 A1 | 11/2002 |
| AU | 2015201538 A1 | 4/2015 |

(Continued)

OTHER PUBLICATIONS

Jeffrey D. Falk, Joseph J. Nagyvary, Exploratory Studies of Lipid-Pectin Interactions, The Journal of Nutrition, vol. 112, Issue 1, Jan. 1982, pp. 182-188, https://doi.org/10.1093/jn/112.1.182 (Year: 1982).*

(Continued)

*Primary Examiner* — Sean E Conley
*Assistant Examiner* — Justin Hwang
(74) *Attorney, Agent, or Firm* — Christensen O'Connor Johnson Kindness PLLC

(57) ABSTRACT

Methods and cleaning compositions for reduction of nucleic acid contamination on surfaces, in air, and in solutions using modified pectin are provided.

13 Claims, 4 Drawing Sheets

Specification includes a Sequence Listing.

(51) Int. Cl.

| | | |
|---|---|---|
| *A61L 9/013* | (2006.01) | |
| *A61L 9/14* | (2006.01) | |
| *C08B 37/00* | (2006.01) | |
| *C11D 7/26* | (2006.01) | |
| *C11D 11/00* | (2006.01) | |
| *C11D 17/04* | (2006.01) | |
| *C12Q 1/6848* | (2018.01) | |
| *A61L 101/50* | (2006.01) | |

(52) U.S. Cl.
CPC .......... *C08B 37/0045* (2013.01); *C11D 7/268* (2013.01); *C11D 11/0041* (2013.01); *C11D 17/049* (2013.01); *C12Q 1/6848* (2013.01); *A61L 2101/50* (2020.08); *A61L 2202/24* (2013.01); *A61L 2209/21* (2013.01)

(56) References Cited

U.S. PATENT DOCUMENTS

| 7,125,842 B2 * | 10/2006 | Kawabe | A61K 45/06 |
|---|---|---|---|
| | | | 514/3.3 |
| 2004/0191790 A1 | 9/2004 | Tomassen et al. | |
| 2005/0163825 A1 | 7/2005 | Naidu | |
| 2006/0127991 A1 | 6/2006 | Christensen et al. | |
| 2011/0054161 A1 | 3/2011 | Bitner | |
| 2013/0072381 A1 | 3/2013 | Trudsoe | |
| 2015/0093755 A1 | 4/2015 | Zhao et al. | |
| 2017/0320764 A1 | 11/2017 | De Boer | |

FOREIGN PATENT DOCUMENTS

| CN | 1798570 A | 7/2006 | | |
|---|---|---|---|---|
| CN | 101232807 1 | 7/2008 | | |
| CN | 101573144 A | 11/2009 | | |
| CN | 103333870 A | 10/2013 | | |
| CN | 107141369 A | 9/2017 | | |
| CN | 108219026 A * | 6/2018 | ............. | A23L 21/15 |
| DE | 69321215 T2 | 6/1999 | | |
| EP | 1613733 A1 | 1/2006 | | |
| WO | 2004/005352 A1 | 1/2004 | | |
| WO | 20040090099 A2 | 10/2004 | | |

OTHER PUBLICATIONS

Mura, P., Mennini, N., Kosalec, I., Furlanetto, S., Orlandini, S., & Jug, M. (2015). Amidated pectin-based wafers for econazole buccal delivery: Formulation optimization and antimicrobial efficacy estimation. Carbohydrate Polymers, 121, 231-240. https://doi.org/10.1016/j.carbpol.2014.11.065 (Year: 2015).*

Office Action dated Apr. 17, 2023, issued in corresponding European Application No. 19766123.4, filed Aug. 16, 2019, 8 pages.

Gerba, C.P. et al., "Microbiological Hazards of Household Toilets: Droplet Production and the Fate of Residual Organisms," Applied Microbiology, vol. 30, No. 2, pp. 229-237, Aug. 1975.

Gibbons, S.M. et al., "Ecological Succession and Viability of Human-Associated Microbiota on Restroom Surfaces," Applied and Environmental Microbiology, vol. 81, No. 2, pp. 765-773, Jan. 2015.

European Patent Office, International Search Report issued in International Application No. PCT/US2019/046925, dated Dec. 4, 2019, 8 pages.

European Patent Office, Written Opinion of the International Searching Authority issued in International Application No. PCT/US2019/046925, dated Dec. 4, 2019, 13 pages.

The International Bureau of WIPO, International Preliminary Report on Patentability issued in International Application No. PCT/US2019/046925, dated Feb. 23, 2021, 14 pages.

Office Action dated Aug. 25, 2022, issued in corresponding Chinese Application No. 201980065427, filed Aug. 16, 2019, 9 pages.

Office Action dated Aug. 31, 2023, issued in corresponding Indian Application No. 202137010965, filed Aug. 16, 2019, 5 pages.

* cited by examiner

SEQUENCE LISTING

<160> NUMBER OF SEQ ID NOS: 4

<210> SEQ ID NO 1
<211> LENGTH: 21

```
<212> TYPE: DNA
<213> ORGANISM: Artificial sequence
<220> FEATURE:
<223> OTHER INFORMATION: Synthetic

<400> SEQUENCE: 1
agcctggatg acaatgactc t                                              21

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
cttatgcatg tccttcttg                                                 19

<210> SEQ ID NO 3
<211> LENGTH: 27
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: N at position 12 is Dabcyl-labeled cytosine

<400> SEQUENCE: 3
cgacggcaac gncaggagga actacga                                        27

<210> SEQ ID NO 4
<211> LENGTH: 126
<212> TYPE: DNA
<213> ORGANISM: Salmo

<400> SEQUENCE: 4
agcctggatg acaatgactc tcagcatctg ccccccctacg ggaactactt ccagaacctg    60
gggggcgacg gcaacgtcag gaggaactac gaactgttgg cctgcttcaa gaaggacatg   120
cataag                                                              126
```

NUCLEIC ACID DECONTAMINATION METHODS

CROSS-REFERENCE(S) TO RELATED APPLICATION(S)

This application claims the benefit of U.S. Provisional Application No. 62/765,014, filed Aug. 17, 2018, which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 70134_Seq_Final_2019-08-14.txt. The text file is 2.23 KB; was created on Aug. 14, 2019; and is being submitted via EFS-Web with the filing of the specification.

FIELD OF THE INVENTION

The invention relates to methods and cleaning compositions for reduction of nucleic acid contamination on surfaces, in air, and in solutions.

BACKGROUND

The use of nucleic acid amplification-based techniques, such as polymerase chain reaction (PCR), has become widespread in various molecular biology applications and in the clinical diagnostics. Unfortunately, the high sensitivity of these techniques makes them vulnerable to contamination. Nucleic acid cross-contamination in the laboratory presents a serious problem for highly sensitive amplification-based assays. The repeated amplification of the target sequence itself, which leads to accumulation of amplification products, or so called amplicons, in the laboratory environment, is of the largest sources of cross-contamination. Prevention of amplicon carryover and/or sterilization of the generated amplicons by destroying them or rendering them ineligible for amplification are critical in molecular biology and diagnostic applications.

Previously reported methods of decontamination typically employ difficult to handle, corrosive reagents, such as solutions of sodium hypochlorite or psoralens. In a large number of cases, additional steps which involve cleaning the decontamination reagent residue are also required. Amplicon decontamination solutions and methods suitable for use in sensitive environments do not always produce reliable results. (Fischer M. et al, Efficacy Assessment of Nucleic Acid Decontamination Reagents Used in Molecular Diagnostics Laboratories, *PLOS One*, Jul. 13, 2016). It is suggested that many of the commonly available compositions, such as Eliminase and DNA Away™, and in some cases bleach, do not consistently and effectively degrade amplifiable nucleic acids and only partially remove the contaminating nucleic acids from surfaces. Moreover, bleach and similar reagents are inadequate to selectively remove nucleic acids from solutions when keeping other biomolecules intact is desirable. Thus, there is a need for improved, inexpensive nucleic acid decontamination methods that employ easy to use, stable reagents and that are compatible with a wide variety of substrates and surfaces.

SUMMARY

In one aspect, provided herein is a method of reducing nucleic acid contamination on a surface comprising contacting a surface contaminated with a nucleic acid with a composition comprising a modified pectin, wherein the modified pectin comprises a plurality of amino groups.

In some embodiments, the modified pectin is an amidated pectin. In some embodiments, the modified pectin comprises one or more monomeric units represented by Formula:

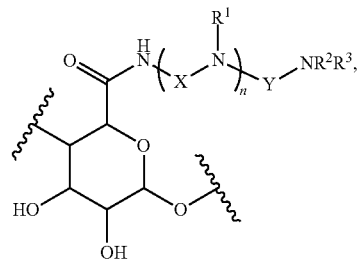

an isomer, a salt, or a tautomer thereof,
wherein:
n is 0, 1, 2, or 3;
$R^1$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^2$ and $R^3$ are independently H or $C_1$-$C_3$ alkyl.

In some embodiments, the molecular weight of the amidated pectin is between about 0.5 kDa and about 500 kDa or between about 100 kDa and about 300 kDa.

In some embodiments, the amidated pectin is in solution at a concentration of about 0.001% to about 5%, about 0.01% to about 1%, or about 0.1% and about 0.5%. In some embodiments, the amidated pectin is in solution with a concentration of about 0.1 µg/mL to about 1,000 µg/mL, about 1 µg/mL to about 500 µg/mL, or about 1 µg/mL to about 100 µg/mL.

In some embodiments, the amidated pectin is amidated citrus pectin or amidated apple pectin.

In some embodiments, the composition is present on a swab, wipe, cloth, filter, pad, or sponge. In some embodiments, the surface is a surface of an instrument or a laboratory bench surface.

In another aspect, provided herein is a method for reducing nucleic acid contamination in a solution, comprising: contacting a solution contaminated with a nucleic acid with a solid support comprising a modified pectin covalently bound thereto, wherein the modified pectin comprises a plurality of amino groups.

In some embodiments, the modified pectin is an amidated pectin. In some embodiments, the modified pectin, e.g., amidated pectin, comprises one or more monomeric units represented by Formula:

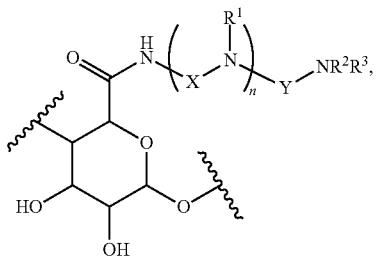

its tautomers, isomers, or salts,
wherein
n is 0, 1, 2, or 3;
$R^1$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^2$ and $R^3$ are independently H or $C_1$-$C_3$ alkyl.

In some embodiments, the solid support is a magnetic bead, glass bead, polystyrene bead, polystyrene filter, or glass filter. In some embodiments, the solid support is a swab, wipe, cloth, filter, or sponge.

In another aspect, provided herein method of reducing aerosolized nucleic acid contamination in air, comprising contacting air contaminated with aerosolized nucleic acid with a composition comprising a modified pectin, wherein the modified pectin comprises a plurality of amino groups.

In some embodiments, the modified pectin is an amidated pectin. In some embodiments, the modified pectin, e.g., amidated pectin, comprises one or more monomeric units represented by Formula:

its tautomers, isomers, or salts,
wherein
n is 0, 1, 2, or 3;
$R^1$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^2$ and $R^3$ are independently H or $C_1$-$C_3$ alkyl.

In some embodiments, the contacting comprises passing the contaminated air through an aqueous composition comprising the modified pectin, e.g. a solution or suspension of the amidated pectin in water. In some embodiments, the contacting comprises passing the contaminated air through a filter comprising the amidated pectin. In some embodiments, the amidated pectin is covalently bound to the filter.

In some embodiments, the nucleic acid is a product of nucleic acid amplification reaction. In some embodiments, the amplification reaction is a polymerase chain reaction.

In some embodiments, the amidated pectin is a pectin comprising one or more monomeric units represented by formula:

an isomer, a salt, or a tautomer thereof.

In some embodiments, the amidated pectin comprises one or more monomeric units represented by formula:

an isomer, a salt, or a tautomer thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
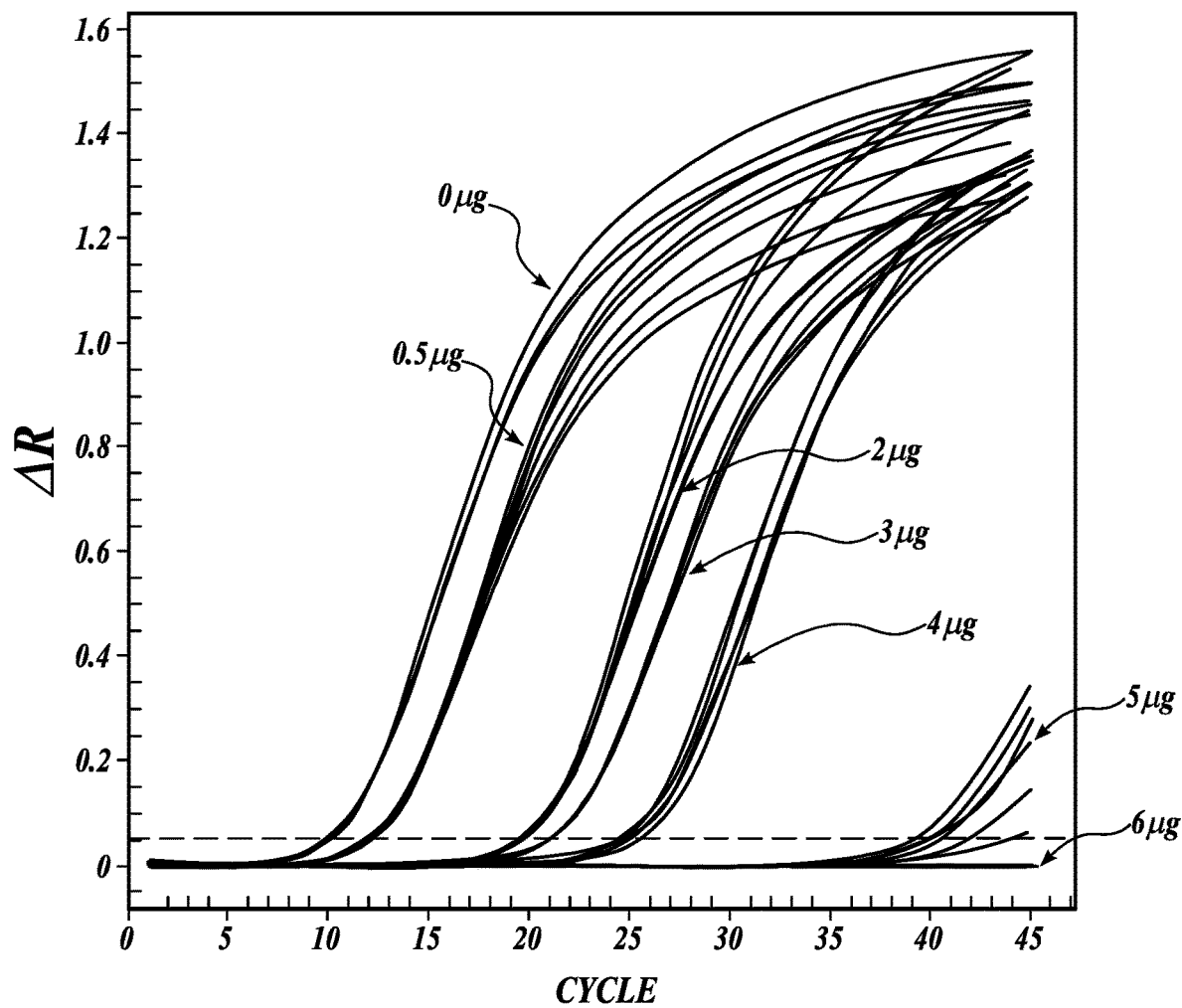
FIG. 1 is an amplification plot of amplicon DNA post treatment with various amounts of an exemplary polyamine modified polysaccharide (spermine-pectin).

In one aspect, the present invention provides a method of reducing nucleic acid contamination on a surface by contacting the surface to be decontaminated with a decontaminating agent comprising a modified pectin, e.g., an amidated pectin, comprising a plurality of amino groups. Preferably, the amidated pectin comprises groups derived from polyamines. In some embodiments, the amidated pectin is a pectin amidated with a polyamine. Without being bound by mechanism or theory, the amidated pectin compounds disclosed herein are believed to facilitate flocculation of nucleic acids, the process by which individual molecules of nucleic acids aggregate or precipitate into small particles when bound to the modified, e.g., amidated pectins, thus rendering the nucleic acids unsuitable for amplification. The decontaminating agents can be used in the form of a solution, a suspension, or can be bound to a solid support, such as a wipe or a sponge.

As used herein, "decontamination" or "reducing nucleic acid contamination" means altering a nucleic acid in a way that makes it no longer capable of or less capable of acting as a template in an amplification reaction compared to a non-altered nucleic acid. Decontamination generally renders the nucleic acids incapable or less capable of interfering with other amplification reactions. In some embodiments, decontamination also means rendering the surfaces to be decontaminated substantially free of nucleic acid contaminants. "Substantially free of nucleic acid contaminants," as used herein, is used to mean that the contaminating nucleic acid is unamplifiable and/or present at a concentration that cannot be detected by amplification-based nucleic acid detection methods.

As used herein, "agent" and "reagent" can be used interchangeably when referred to the decontaminating compositions, unless indicated otherwise.

In some embodiments, "reducing contamination" or "decontamination" refers to reducing the ability of or preventing the nucleic acid from binding to another nucleic acid, protein, or other biological substance. Reducing nucleic acid contamination or nucleic acid decontamination also refers to preventing or making the nucleic acids less capable of serving as a substrate for an enzyme. Reducing nucleic acid contamination or nucleic acid decontamination, as used herein, does not refer to any particular mechanism by which the reduction in contamination, or decontamination, occurs.

Modified Pectins

In some embodiments, the decontaminating agents disclosed herein comprise a modified polysaccharide. In some embodiments, the polysaccharides are pectins. Pectins are naturally occurring complex polysaccharides typically found in plant cell walls. Pectins comprise an alpha 1-4 linked polygalacturonic acid backbone intervened by rhamnose residues and modified with neutral sugar side chains and non-sugar components such as acetyl, methyl, and ferulic acid groups. The galacturonic acid residues in pectin are partly esterified and present as the methyl esters. The degree of esterification is defined as the percentage of carboxyl groups esterified. Pectins with a degree of esterification, e.g., above 50%, are classified as high methyl ester ("HM") pectins or high ester pectins, and pectins with a degree of esterification lower than 50% are referred to as low methyl ester ("LM") pectins or low ester pectins. Most pectin found in fruits and vegetables are HM pectins.

As used herein, "amidated pectin" refers to any naturally occurring pectin that has been structurally modified, e.g., by chemical, physical, or biological (including enzymatic) means, or by some combination thereof, wherein some of the ester or acid groups have been converted to amide groups. Amidated pectins can be prepared by contacting unmodified pectin with a solution of a suitable amine thereby converting the ester groups of the unmodified pectin to amides.

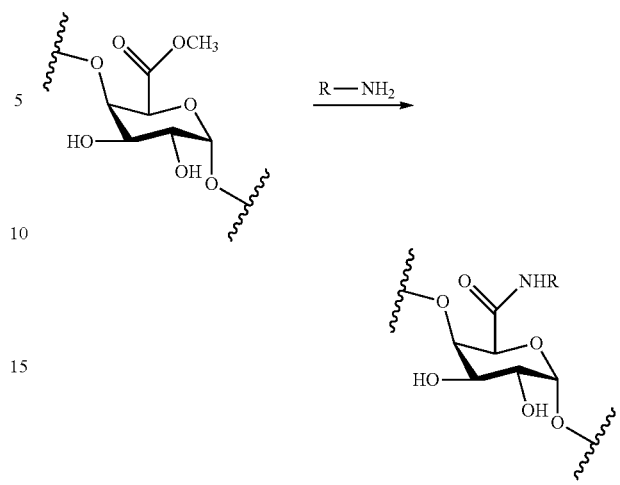

Alternatively, unmodified pectin or hydrolyzed pectin, including partially hydrolyzed pectin, can be reacted with an amine in the presence of a suitable coupling agent to form amidated pectin. Non-limiting examples of suitable coupling agents include carbodiimide coupling agents such as EDC and EDCI, phosphonium and imonium type reagents such as BOP, PyBOP, PyBrOP, TBTU, HBTU, HATU, COMU, and TFFH.

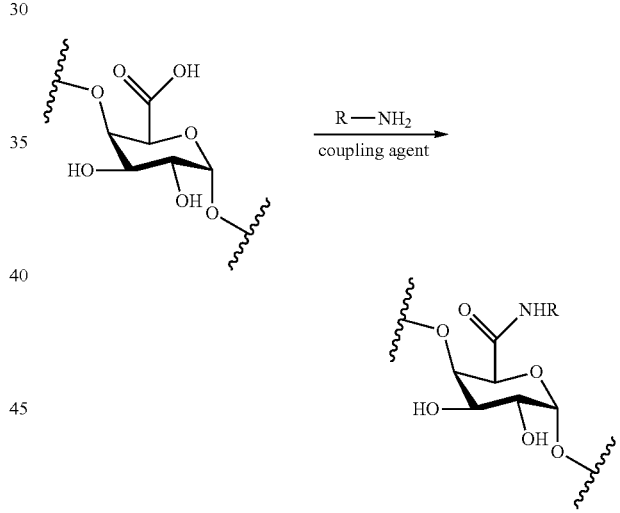

A modified, e.g., amidated pectin can be obtained by any of the methods described herein. Particularly useful starting materials for synthesis of modified pectins include fruit pectins, for example, apple and citrus pectins. In some embodiments, the precursor (unmodified) pectins have relative molecular weights between about 5 kDa and about 1,100 kDa, between about 10 kDa and about 500 kDa, between about 10 kDa and about 300 kDa, between about 20 kDa and about 200 kDa, or between about 20 kDa and about 100 kDa. In some embodiments, the polysaccharide agents have relative molecular weights between about 120 kDa and about 300 kDa, between about 150 kDa and about 300 kDa, or between about 120 kDa and about 175 kDa. In some embodiments, the relative molecular weights of the amidated pectins can be determined by size exclusion chromatography using a molecular weight standard, such as Pullulan series standards, as a reference.

In some embodiments, the decontaminating reagents disclosed herein comprise an amidated pectin comprising one or more monomeric units substituted with at least one amino group. In some embodiments, the amidated pectins comprise one or more monomeric units having the structure of Formula I:

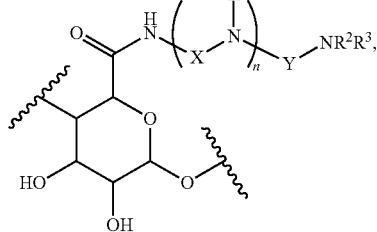

(I)

wherein:

n is 0, 1, 2, or 3;

$R^1$ is H or $C_1$-$C_3$ alkyl;

X, at each occurrence, is independently $C_2$-$C_4$ alkylene or $C_4$-$C_6$ heteroalkylene;

Y is a $C_2$-$C_3$ alkylene or $C_4$-$C_6$ heteroalkylene; and $R^2$ and $R^3$ are independently H or $C_1$-$C_3$ alkyl.

In some embodiments, the amidated pectins comprise one or more monomeric units represented by Formula II:

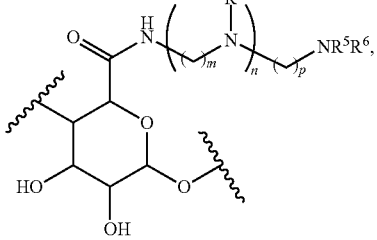

(II)

its isomers, tautomers, and combinations thereof, wherein:

n is 0, 1, 2, or 3;

m, at each occurrence, is independently 2, 3, or 4;

p is 2, 3, or 4;

$R^4$ is H or $C_1$-$C_3$ alkyl; and $R^5$ and $R^6$ are independently H or $C_1$-$C_3$ alkyl.

In some embodiments, the amidated pectin comprises one or more monomeric units comprising a primary amino group. In some embodiments, the amidated pectin is amidated with a polyamine. As used herein, a polyamine is a compound comprising two or more amino groups. Polyamines that can be used for modification of pectins of the solid supports disclosed herein include both synthetic polyamines and naturally occurring polyamines, e.g., spermidine, spermine, putrescine. In some embodiments, the polyamine is selected from spermine, spermidine, cadaverine, ethylenediamine, and putrescine. In some embodiments, the polyamine is spermine or spermidine.

In some embodiments, the amidated pectin comprises one or more units having the structure of Formula III or Formula IV, including their isomers and tautomers:

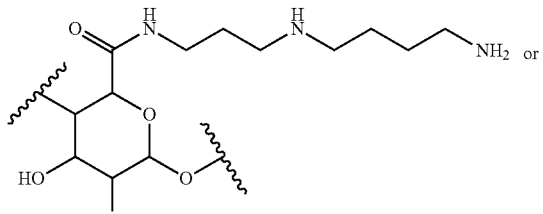

(III)

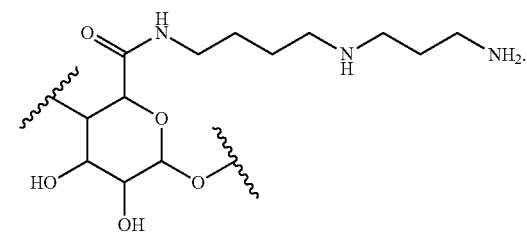

(IV)

In some embodiments, the amidated pectin comprises one or more monomeric units represented by formula:

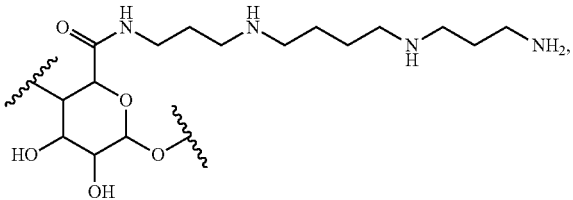 [SMILES: *OC1OC(C(=O)NCCCNCCCCNCCCN)C(*)C(O)C1O]

(V)

an isomer, a salt, or a tautomer thereof.

In some embodiments, the modified polysaccharide is a pectin that was obtained by periodate oxidation of an unmodified pectin followed by reductive amination, e.g., reductive amination with a polyamine. Methods of periodate oxidation and reductive amination of carbohydrates are known in the art.

As used herein, the terms "alkyl," "alkenyl," and "alkynyl" include straight-chain, branched-chain, and cyclic monovalent hydrocarbyl radicals, and combinations thereof, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms, it can be represented as 1-10C, C1-C10, $C_1$-$C_{10}$, $C_{1-10}$, or C1-10. The term "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain plus the number of such heteroatoms that are included as replacements for carbon atoms in the cycle or chain being described.

A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl, and alkynyl groups can be optionally substituted to the extent that such substitution makes sense chemically. Typical substituents include, but are not limited to, halogens (F, Cl, Br, I), =O, =NCN, =NOR, =NR, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halogens (F, Cl, Br, I), =O, =NCN, =NOR', =NR', OR', $NR'_2$, SR', $SO_2R'$, $SO_2NR'_2$, $NR'SO_2R'$, $NR'CONR'_2$, NR'C(O)OR', NR'C(O)R', CN, C(O)OR', C(O)$NR'_2$, OC(O)R', C(O)R', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl, and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" can be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples of aryls include phenyl and naphthyl. Similarly, "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-14 ring member atoms. Typically, monocyclic heteroaryls contain 5-6 ring members, and bicyclic heteroaryls contain 8-10 ring members.

Aryl and heteroaryl moieties can be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group can be further substituted with the groups described herein as suitable for each type of such substituents or for each component of the substituent. Thus, for example, an arylalkyl substituent can be substituted on the aryl portion with substituents described herein as typical for aryl groups, and it can be further substituted on the alkyl portion with substituents described herein as typical or suitable for alkyl groups.

"Optionally substituted," as used herein, indicates that the particular group being described can have one or more hydrogen substituents replaced by a non-hydrogen substituent. In some optionally substituted groups or moieties, all hydrogen substituents are replaced by a non-hydrogen substituent (e.g., a polyfluorinated alkyl such as trifluoromethyl). If not otherwise specified, the total number of such substituents that can be present is equal to the number of H atoms present on the unsubstituted form of the group being described. Where an optional substituent is attached via a double bond, such as a carbonyl oxygen or oxo (=O), the group takes up two available valences, so the total number of substituents that may be included is reduced according to the number of available valences.

In some embodiments, the decontaminating reagent comprises a solution of an amidated pectin having one or more monomeric units represented by formula:

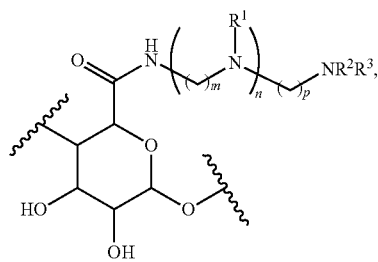

its tautomers, its isomers, or salts, wherein:

n is 0, 1, 2, or 3;

m is 2, 3, or 4;

p is 2, 3, or 4; and $R^1$, $R^2$, and $R^3$ are independently H or $C_1$-$C_3$ alkyl.

In some embodiments, the amidated pectin comprises one or more primary amino groups. In some embodiments, the amidated pectin is amidated with a polyamine. In some embodiments, the polyamine is selected from spermine, spermidine, cadaverine, ethylenediamine, and putrescine.

In some embodiments, the amidated pectin comprises one or more units represented by formulas:

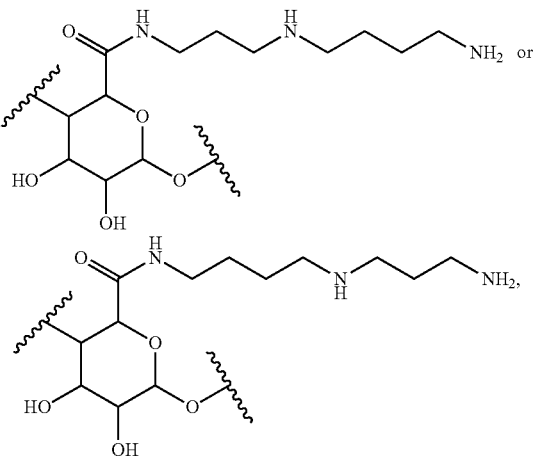

their tautomers, isomers, salts, or combinations thereof.

In some embodiments, the amidated pectin comprises one or more monomeric units represented by formula:

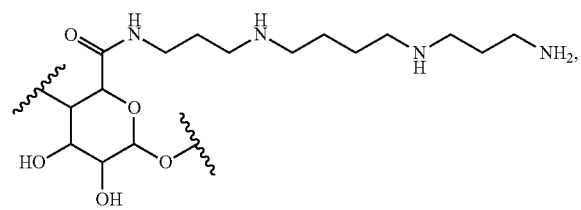 [SMILES: *OC1OC(C(=O)NCCCNCCCCNCCCN)C(*)C(O)C1O]

an isomer, a salt, or a tautomer thereof.

In some embodiments, the amidated pectins comprise a plurality of monomeric units represented by formulae shown above. As used herein, the term "plurality" means more than one. For example, a plurality of monomeric units means at least two monomeric units, at least three monomeric units, or at least monomeric units, and the like. If an embodiment of the present invention comprises more than one types of monomeric units, they may also be referred to as a first monomeric unit, a second monomeric unit, a third monomeric unit, etc.

Decontaminating Methods

In one aspect, disclosed herein are the method for reducing nucleic acid contamination on a surface, comprising: contacting the surface to be decontaminated with a solution comprising a dissolved or suspended modified pectin comprising a plurality of amino groups, e.g., an amidated pectin. In some embodiments, the modified pectin is an amidated pectin, wherein the amidated pectin comprises one or more monomeric units having the structure of Formulae I-V. In other embodiments, the concentration of the amidated pectin in the decontaminating solution is between about 0.01% and about 5%, between about 0.01% and about 1%, between about 0.01% and about 0.1%, between about 0.1% and about 5%, between about 0.1% and about 1%, between about 0.5% and about 5%, or between about 0.5% and about 2%. In some embodiments, concentration of the amidated pectin in the decontaminating solution is between about 0.1 µg/mL and about 10,000 µg/mL, between about 0.1 µg/mL and about 5,000 µg/mL, between about 0.1 µg/mL and about 1,000 µg/mL, between about 0.1 µg/mL and about 100 µg/mL, between about 0.1 µg/mL and about 5 µg/mL. A person skilled in the art can select the suitable amount and/or concentration of the decontaminating pectin depending on the amount of nucleic acid contaminant to be removed.

In some embodiments, the decontaminating compositions disclosed herein, for example, solutions or suspensions of amidated pectins, are stable upon storage at room temperature.

In some embodiments, the decontaminating compositions can further comprise additives such soaps, detergents, disinfecting agents, and/or other suitable chemicals. Examples of suitable disinfecting agents may include, for example, quaternary ammonium compounds, colloidal silver, acetic acid, hydrogen peroxide, or a combination thereof.

In some embodiments, the decontaminating solution is present on a swab, wipe, cloth, filter, or sponge. In particular embodiments, the surface to be decontaminated is a surface of an instrument or a laboratory bench surface. In other embodiments, the solution is used to decontaminate laboratory pipettes.

In some embodiments, the methods of decontamination disclosed herein further comprise rinsing or wiping the surface to be decontaminated with water or another solution that does not comprise an amidated pectin.

In some embodiments, the methods further comprise contacting the surface or solution to be decontaminated from nucleic acid contaminants with a solution comprising a metal ion that can form a hydrogel with pectin thereby precipitating, trapping, complexing, or otherwise render insoluble the nucleic acid or the complex of the nucleic acid with the amidated pectins of the decontaminating solutions disclosed herein. Suitable metal ions include $Ca^{2+}$ and $Mg^{2+}$ ions. Any metal that can crosslink a pectin or an amidated pectin is suitable to be included in the decontaminating compositions disclosed herein.

In another aspect, provided herein are methods for reducing nucleic acid contamination in solution, comprising: contacting the solution to be decontaminated with composition comprising an amidated pectin covalently bound to a solid support, wherein the amidated pectin comprises a plurality of monomeric residues having the structure of Formulae I-V shown above. As used herein, the term "solid support" refers to any substrate including paramagnetic particles, gels, controlled pore glass, magnetic beads, microspheres, nanospheres, capillaries, filter membranes, columns, cloths, wipes, paper, flat supports, multi-well plates, porous membranes, porous monoliths, wafers, combs, or any combination thereof. Solid supports can comprise any suitable material, including but not limited to glass, silica, titanium oxide, iron oxide, ethylenic backbone polymers, polypropylene, polyethylene, polystyrene, ceramic, cellulose, nitrocellulose, and divinylbenzene.

Covalent attachment of modified pectins such as amidated pectins to solid supports can be achieved in any suitable manner by reacting the pectin with a solid support that comprises amine-reactive groups, for example, an epoxide, aldehyde, ketone, or activated ester.

In some embodiments, the amidated pectins of the disclosure are covalently attached to the solid supports via an amide bond, e.g., an amide bond formed between a carboxy group of the solid support and an amino group of the amidated pectin. Formation of the amide bond can be carried out by any suitable methods. For example, amidated pectin comprising one or more primary amino groups can be reacted with a substrate comprising one or more carboxylic acid groups in the presence of a suitable coupling agent. Non-limiting examples of suitable coupling agents include carbodiimide coupling agents such as DCC and EDCI, phosphonium and imonium type reagents such as BOP, PyBOP, PyBrOP, TBTU, HBTU, HATU, COMU, and TFFH. In some preferred embodiments, the carboxylic acid group of the solid substrate can be converted to an activated ester and then subsequently reacted with an amino group of the amidated pectin.

In some embodiments, the solid supports comprise a compound of any one of Formulae I-V covalently attached to the solid support.

In some embodiments, the amidated pectins are incorporated into a cloth, sponge, pad, or wipe by impregnating or coating said cloth, sponge, pad, or wipe with the amidated pectin. Examples include, but are not limited to cotton swabs, woven fiber pads, or wipes typically used for laboratory purposes, such as KimWipes™, manufactured by Kimberly-Clark Corporation.

In another aspect, provided herein is a method of reducing aerosolized nucleic acid contamination in air, comprising contacting air contaminated with aerosolized nucleic acid with a composition comprising a modified pectin, e.g., an amidated pectin comprising one or more monomeric units of any one of Formulae I-V or combinations thereof. In some embodiments, contacting the air contaminated with aerosolized nucleic acid comprises passing the air through a solution or a suspension of the amidated pectin. In some embodiments, contacting the air contaminated with aerosolized nucleic acid comprises passing the air through a filter comprising the amidated pectin. In some embodiments, the amidated pectin is covalently bound to the filter. In some embodiments, contacting the air contaminated with aerosolized nucleic acid comprises passing the air above a surface comprising the amidated pectin covalently bound thereto. In some embodiments, the amidated pectin is a pectin amidated with spermine, e.g., by NHS/EDC coupling, or by sequential oxidation of a pectin with periodate and reductive amination with an amine, e.g., spermine, and sodium borohydride.

Nucleic acid contaminants also can be present in the form of aerosols or upon dust particles. Thus, air filters comprising an amidated pectin of the invention can be useful for the removal of such contaminants. In some embodiments, such filters can be prepared, for example, by dipping the filter material into a solution containing the amidated pectin of the invention and then drying the filter. In other embodiments, the filter material can be covalently coated with the amidated pectins.

In some embodiments, it is advantageous to remove a nucleic acid contaminant form a solution. In such embodiments, the solution comprising the contaminant can be treated with a composition comprising an amidated pectin of the invention, for example, a solid support comprising an amidated pectin covalently attached to the solid support. In some embodiments, such treatment includes passing the solution to be decontaminated through a filter, a monolith, a membrane, or the like. In other embodiments, the solution to be decontaminated is contacted with a solid support, for example, a magnetic bead.

In some embodiments, the nucleic acid contaminant is an amplicon. In some embodiments, compositions comprising the amidated pectins are used to remove amplicon contamination and/or to prevent said contamination of molecular diagnostics laboratory surfaces, instrumentation, and equipment. The decontamination of such surfaces, instrumentation, or equipment can be carried out in any suitable manner, for example, using any of the methods described above. In some embodiments, the decontaminating solutions disclosed herein are added to an amplification reaction after completion of the amplification reaction and detection of the product of the amplification, thereby rendering the product of the amplification, e.g., an amplicon, substantially unamplifiable. In some embodiments, the decontaminating solution is added to the amplification reaction post-amplification in an automated cartridge. The decontaminating agents disclosed herein have certain advantages because, unlike bleach or other oxidants that can react with certain components of molecular diagnostics tests with a release of toxic byproducts, the decontaminating agents do not react with such components.

The decontaminating performance of the compositions disclosed herein can be tested using any suitable method, e.g., a wipe test. In some embodiments, any methods of efficacy assessment of decontamination reagents disclosed in the literature can be used (see, e.g., Fischer M. et al, Efficacy Assessment of Nucleic Acid Decontamination Reagents Used in Molecular Diagnostics Laboratories, *PLOS One*, Jul. 13, 2016).

Preferred embodiments of this invention are described herein, including the best mode known to the inventors for carrying out the invention. Variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While exemplary embodiments have been illustrated and described, it will be appreciated that various changes can be made therein without departing from the spirit and scope of the invention. While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

EXAMPLES

Example 1. Preparation of Amidated Pectins

Synthesis of Spermine-Pectin Conjugate Compound 1

Apple pectin (10.0 g) was added to 1 L of Milli-Q filtered water and stirred for 1 h. 5 M NaOH (10 mL) was added, stirred for another 20 min, and then 1 N HCl (30 mL) was added (pH=4.2). N-(3-dimethylaminopropyl)-N'-ethylcarbodiimide hydrochloride (EDC, 10.08 g, 52.59 mmol) and N-hydroxysuccinimide (NHS, 3.026 g, 52.59 mmol) were added to the solution and stirred at RT for 1 h. Spermine (80 mL, 368 mmol) was added and the solution was stirred for 22 h at RT. The solution was then poured into rapidly stirring MeOH (2 L) and stirred for 20 min. The solids were collected by filtering the solution through a medium fitted glass funnel, and then washed with MeOH two times. The solids were dried under vacuum for 40 h at 50° C. The solids were ground to a fine powder using an electric coffee grinder and suspended in 500 mL of an acid wash solution (55% isopropyl alcohol, 34.5% water, and 10.5% concentrated hydrochloric acid) and stirred for 4.5 h. The solution was filtered off, and the solids were washed additionally twice with acid wash solution and then dried under vacuum overnight at 50° C. The solids were suspended in 750 mL of DI water and centrifuged at 4200 rpm using 50 mL centrifuge tubes for 10 min. Supernatants were collected and combined. The pellets were combined and suspended in 350 mL of DI water and centrifuged for 17 h at 4200 rpm using 50 mL centrifuge tubes. The supernatants were combined with the first supernatants. All of the combined supernatants were filtered through a 2-micron filter. The filtered solution was dried by lyophilization giving 7.78 g of spermine-pectin conjugate. Anal. Calc for $C_{16}H_{32}N_4O_5$ (galacturonic acid monomer plus spermine): C, 53.3; H, 8.95; N, 15.5. Found: N, 7.21.

Synthesis of Spermine Conjugate Compound 2 by Oxidative Cleavage of Pectin Followed by Reductive Amination In this example, a general procedure is provided for the modification of polysaccharide polymers with various polyamines through oxidation followed by reductive amination.

(A). Oxidation. Apple pectin (2.5 g) was added in portions to 250 mL deionized water with magnetic stirring until it has all dissolved. To this was added potassium periodate 2.43 g in portions with stirring and left stirring for 18 h. Reaction mixture was then dialyzed against water through 8 MWCO dialysis tubing over three. The resulting desalted polymer was subsequently lyophilized to give oxidized pectin as a crunchy off-white solid. The concentration of aldehydes can be readily measured via hydroxylamine titration (described in Zhao, H.; Heindel, N. D. *J. Pharm. Res.* 8(3), 400-402.) Aldehyde content determined to be 4.9 mmol/g (~1 eq aldehyde per polymer unit).

(B). Reductive amination. Oxidized pectin from step A (1.0 g) was suspended in 100 mL of deionized water, added spermine (1.32 g, 1.25 eq) and let stir for 18 h at room temperature. Added 1 g sodium borohydride pellet to the reaction and let stir for 18 h. The reaction mixture was then dialyzed against water through 8 kd MWCO dialysis tubing over three days and subsequently lyophilized to yield 200 mg of Compound 2 as off-white fluffy solid.

Preparation of Spermine-Pectin Conjugate Solutions

Solutions (1%, w/w) of spermine-pectin conjugates Compound 1 and Compound 2 were prepared by dissolving 1.0 g of the lyophilized spermine-pectin conjugates Compound 1 or Compound 2 in 100 mL of Milli-Q filtered water and removing any insoluble particles by using centrifuge.

The 0.1%, 0.01%, 0.001% and 0.0001% dilutions in water were prepared from 1% solution.

Example 2 Preparation of Functionalized Beads

A Synthesis of Spermine-Pectin Conjugate

Apple pectin (2.45 g) was slowly added to 250 mL of rapidly stirred Milli-Q filtered water. The solution was stirred until the pectin was thoroughly wetted (1.5 h). 2.5 M NaOH (~5 mL) was added until the pH of the solution was 12. The solution was stirred for 30 min, and then 1 N HCl (~7 mL) was added until the pH 9. N-(3-dimethylaminopropyl)-N'-ethylcarbodiimide hydrochloride (2.45 g, 12.8 mmol) and N-hydroxysuccinimide (1.45 g, 12.6 mmol) were added to the solution, and the mixture was stirred at RT for 1.25 h. Spermine (25.0 g, 124 mmol) was added and the solution was stirred overnight at RT. The solution was then poured into rapidly stirring MeOH (1.5 L) and stirred for 45 min. The solids were collected by filtering the solution through a medium fritted glass funnel, and then washed with MeOH three times. The solids were dried under vacuum overnight at 50° C. The solids were ground to a fine powder using a mortar and pestle and the powder was placed in in 50 mL of an acid wash solution (55% isopropyl alcohol, 34.5% water, and 10.5% concentrated hydrochloric acid) which was then stirred for 1 h. The solids were filtered off and washed with more acid wash solution (5×) and a neutral wash solution (59% isopropyl alcohol and 41% water) five times. Then the solids were washed with MeOH (5×) and dried under high vacuum to yield 2.20 g of the spermine-pectin conjugate. Anal. Calcd for $C_{16}H_{32}N_4O_5$ (galacturonic acid monomer plus spermine): C, 53.3; H, 8.95; N, 15.5. Found: C, 39.0; H, 6.58; N, 4.07.

B Modification of Beads

The following beads were modified with the pectins described above:
- Silica Microspheres, Carboxyl, 1.0 μm (Polysciences, Warrington, PA, 24754-1)
- Carboxyl-polystyrene Particles, 5.11 μm (Spherotec, Germany, CP-50-10)
- NHS-Activated Sepharose 4 Fast Flow (Sepharose beads, GE healthcare, Chicago, IL, 17-0906-01)

For Sepharose beads, NHS-activated bead form was used, so EDC/NHS activation was not performed. Hydrolyzed NHS-sepharose beads were used as non-modified bead controls. In this Example, a procedure is provided for functionalization of carboxyl-modified beads with amine containing pectin polymer, such as the modified pectin described above.

Polystyrene beads (~5 micron, 2 mL of 5% wt suspension) modified with carboxyl groups (Spherotec, CP-50-10) were diluted with DI water (4 mL) and sonicated for 15 min. To the bead suspension, 40 mg of EDC·HCl and 40 mg of NHS were added. The suspension was stirred for 24 h for activation, briefly centrifuged at 4000 rpm for 5 min and the supernatant decanted. Beads were resuspended in 5 ml DI water, and to this was added a 1% solution of amine polymer (5 mL). Amine pectin polymer solution was prepared by stirring amine pectin polymer in DI water for 18 h, and then centrifugation at 9000 rpm for 30 min to remove any dissolved material. Suspension was stirred for 18 h, then centrifuged at 9000 rpm for 30 min, diluted with 45 mL of water and rinsed in the same manner. The process was repeated with 0.1 M NaOH (1×), 0.1 M HCl (1×), and DI water (2×). Beads were resuspended in 5 ml DI H2O, sonicated for 30 min, and concentration measured by weighing the amount of beads in a 150 ul aliquot via Speedvac.

Example 3 Decontamination of Nucleic Acids

Experiment A

Seven separate sample vials were prepared, each containing 2.5 ng of the salmon dsDNA (126 bp) amplicon template sequence in 100 µL of water. No spermine-pectin conjugate was added to the first vial. Spermine-pectin conjugate in 10 uL of water was added to each of the remaining vials (0.5, 2, 3, 4, 5 and 6 µg). After sitting at RT for 1 h, 5 µL was removed from each vial and added to the PCR reaction solution (15 µL). Real-time qPCR was performed on a PCRmax Eco 48 using the conditions described below. Thermal cycle was programmed for 60 sec at 95° C., followed by 40 cycles of 95° C. for 10 sec and 60° C. for 60 sec. PCR reaction solution: 25 mM KCl, 50 mM $MgCl_2$, 4.2 mM HEPES, 0.1% Tween, 0.2 mM dNTP's, 1.5 mU/uL of hot start Taq enzyme, 400 nM probe and 400 nM primers.

```
Forward primer:
                                        SEQ ID NO: 1
5'-AGCCTGGATGACAATGACTCT-3'

Reverse primer:
                                        SEQ ID NO: 2
5'-CTTATGCAT GTCCTTCTTG-3'

Probe:
5'-CGACGGCAACG(T-Dabcyl)CAGGAGGAACTACGA-3'
SEQ ID NO: 3 modified with FAM (5') and BHQ (3').
```

Double stranded DNA (126 bp), from a salmon genomic sequence, was purchased from Integrated DNA Technologies to be a model of an amplicon product from PCR. Amplicon template sequence (126-mer):

```
                                        SEQ ID NO: 4
5'AGCCTGGATGACAATGACTCTCAGCATCTGCCCCCCTACGGGAACTAC

TTCCAGAACCTGGGGGGCGACGGCAACGTCAGGAGGAACTACGAACTGTT

GGCCTGCTTCAAGAAGGACATGCATAAG-3'
```

FIG. 1 shows the PCR curves where 2.5 ng of template dsDNA (126 bp) was treated with spermine conjugated pectin. Each curve represents an experiment where 0.5 to 6.0 ng of spermine-pectin was added to 2.5 ng of dsDNA. The first curve on the left side has a Ct of 12.2 which represents the no spermine-pectin control. As more pectin is added to the separate reactions, the Ct's become longer, until at 6 ug of spermine-pectin, no Ct is observed. This is the concentration where all of the template is bound by the spermine-pectin conjugate, and the template cannot be amplified in the PCR reaction.

Experiment B

Two separate vials were prepared each containing 6 µg of the spermine-pectin conjugate in 60 µL of water. To one vial, 4 µg of hgDNA in 20 µL of water was added and allowed to sit at RT for 1 h. 2.5 ng of the salmon dsDNA (126 bp) model amplicon in 100 uL was then added to both vials. A 5 µL aliquot was removed from each vial to use in PCR as described below.

Figure 2:
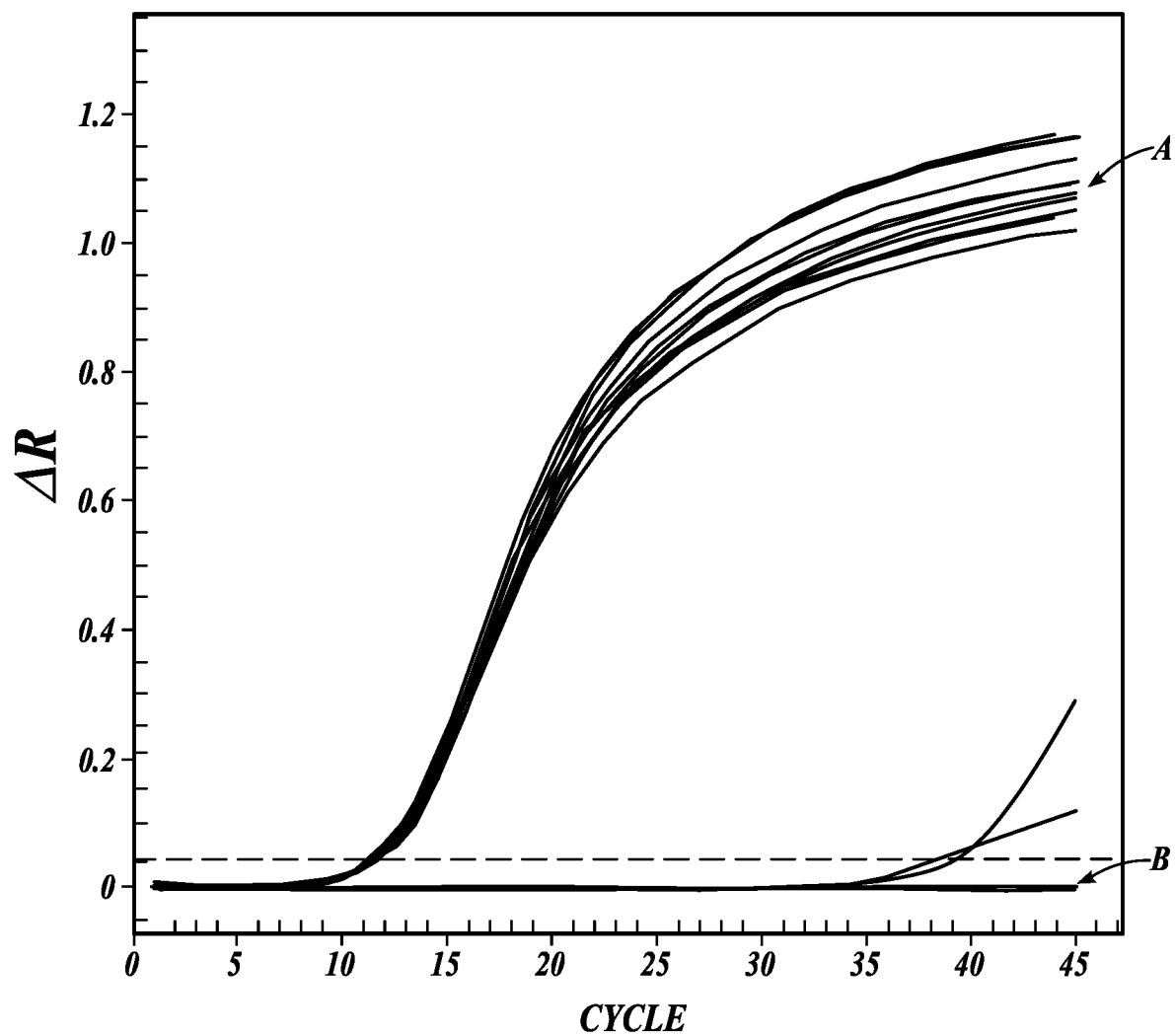
FIG. 2 demonstrates binding of contaminant DNA with an exemplary polyamine modified polysaccharide (spermine-pectin) followed by amplification of target DNA.

When 2.5 ng of salmon dsDNA (126 bp) was treated with 6 ug of the spermine-pectin conjugate, no PCR amplification occurred (FIG. 2). However, if the 6 µg of spermine-pectin was first treated with 4 µg of hgDNA, to represent a DNA contaminate, and then the 2.5 ng of salmon dsDNA was added, a PCR signal was acquired that was the same as the 2.5 ng of salmon DNA only control (FIG. 2). This example shows that the spermine-pectin conjugate can bind-up contaminating DNA first, and that amplification of the desired target DNA will still occur in the presence of the spermine-pectin-contaminate DNA complex.

Experiment C

The salmon dsDNA (126 bp) model amplicon was diluted to a concentration of 10 million copies per 1 mL of water. 1 mL of the DNA solution was added to each of three separate vials. One vial was used as the no spermine-pectin control sample. To the other two vials, 1 µg of the spermine-pectin conjugate in 10 µL of water was added. And to only one of these vials, an additional 2.5 ng of the salmon dsDNA (126 bp) model amplicon was added in 100 µL of water. After sitting for 1 h, 5 µL was used from each vial for the PCR reaction as described below.

Figure 3:
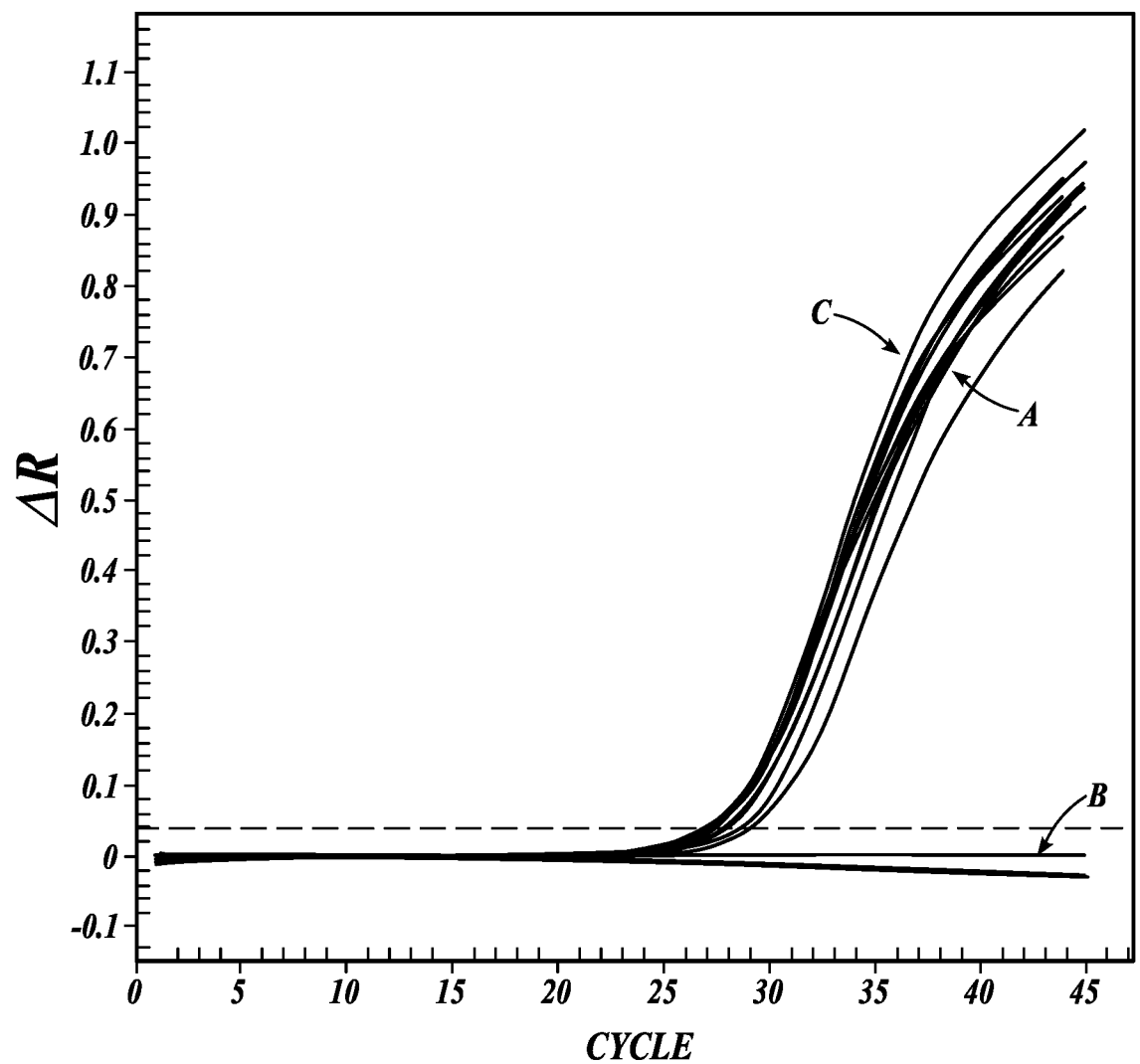
FIG. 3 shows that when 10 million copies of dsDNA (126 bp) were treated with 1 µg of an exemplary spermine-modified polysaccharide, the amplification was completely inhibited (B). After more copies ($1.9 \times 10^{10}$) were added to the spermine-pectin-DNA mixture, the amplification recovered (C) and is comparable to amplification of untreated DNA (A). This shows how the spermine-pectin conjugate can be used to bind minor DNA contaminates, and then allow amplification of target to take place.

FIG. 3 shows that when 10 million copies of dsDNA (126 bp) were treated with 1 µg of the spermine-pectin conjugate, the amplification was completely inhibited (B). After more copies ($1.9 \times 10^{10}$) were added to the spermine-pectin-DNA mixture, the amplification recovered (C), comparable to untreated DNA amplification (A). This shows how the spermine-pectin conjugate can be used to bind minor DNA contaminates, and then allow amplification of target to take place.

Example 4 Decontamination of Surfaces from Amplicon

Preparation of Amplicon Solution

PCR with the salmon DNA target was performed by the method described above without using the probe. After 40 PCR cycles, the content of the PCR tube was diluted 1000 times giving "amplicon solution" with approximately 400B copies of DNA/mL. The ability to amplify and the number of copies/mL were confirmed by parallel comparison in PCR with standard 10K copies of the salmon DNA target. The amplicon solution was used in the following experiments.

Preparation of Dry Amplicon on a Surface

A 31×23 cm polypropylene plate was roughened using P150 (very fine) sandpaper. The surface was cleaned with water, tested for wettability and dried. For some experiments, the surface was marked with a grid of 7.5 cm×1.8 cm spaciously separated segments for testing various treatments and running controls. 10 mL of amplicon solution was deposited onto the dry surface and spread consistently throughout the surface using a cotton swab. The plate was left on a horizontal surface and allowed to dry for 4 hr. The surface containing the dried amplicon was subjected to the following decontaminating and control experiments.

Treatment of Surface Amplicon with Solutions of Compound 1 at Various Concentrations To eight sets of 13.5 cm² segments on the surface containing amplicon was applied 2 mL of 1% solution of Compound 1. The solution was evenly spread between all four segments using cotton swab and let dry overnight on horizontal surface. Wet swabs collected from each segment into 0.5 mL of water and subjected to PCR analysis in triplicates.

The same experiments were performed with 0.1%, 0.01%, 0.001%, 0.0001% Compound 1 solution and 0% control (water). Additional eight segments were left for untreated control. Average Ct values from the swabs and same samples with added 10K DNA targets are presented in Table 1.

TABLE 1

Inactivation of amplicon by Compound 1 solutions

| Sample | Ct | Ct with added 10K DNA |
|---|---|---|
| 0.1% | ND | ND |
| 0.01% | ND | ND |
| 0.001% | 17 | 16 |
| 0.0001% | 16 | 16 |
| Water | 16 | 16 |

Deactivation of Amplifiable Amplicon in Aerosol Form

Figure 4:
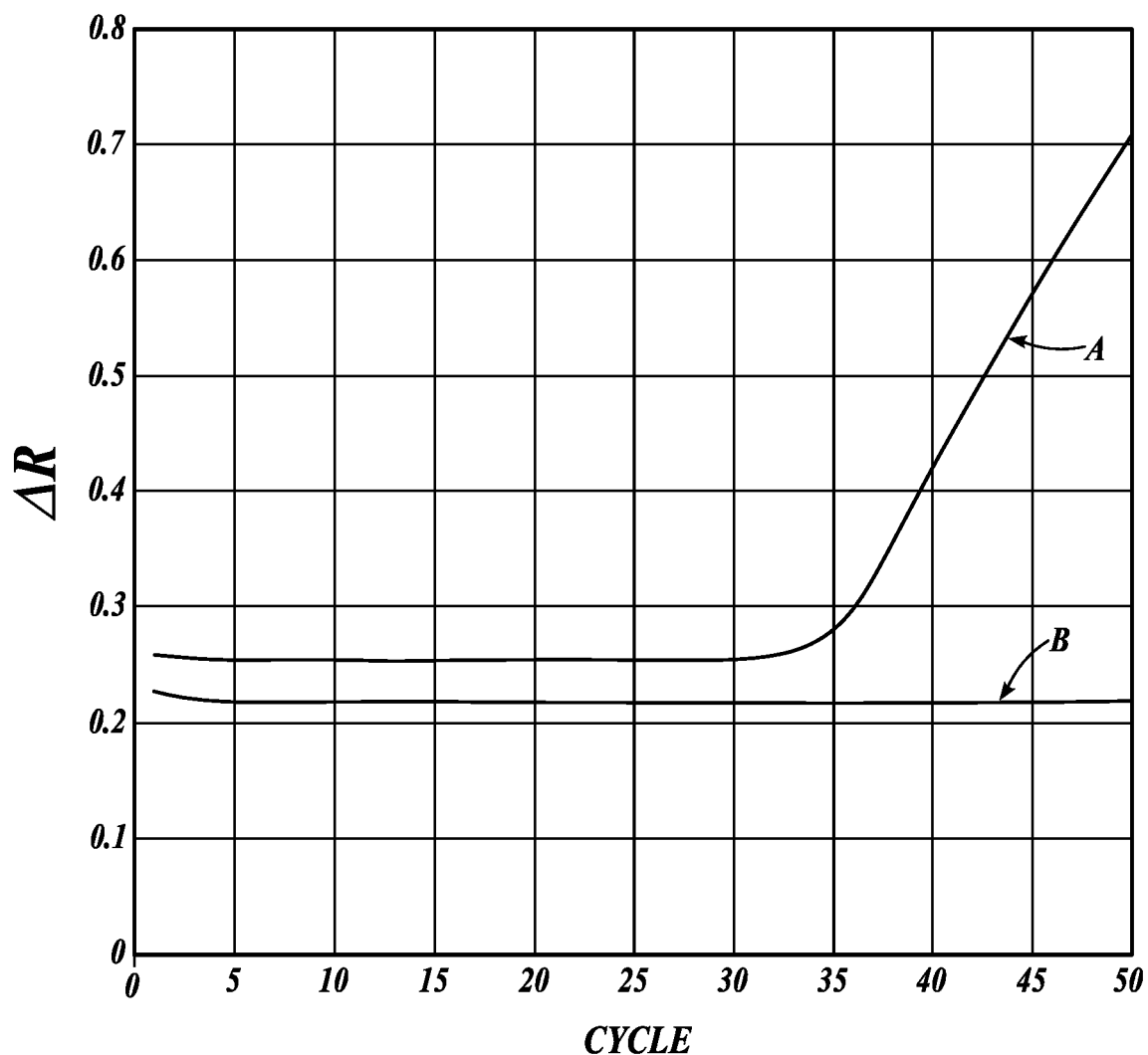
FIG. 4 compares averages of eight PCR runs of two sets of air samples collected over 24 h 3 cm above the surface treated with dry amplicon. Graph (A) is the amplicon on the surface without treatment and graph (B) is the dry surface with amplicon sprayed with 0.1% solution of an exemplary spermine-modified polysaccharide.

Aerosol was collected above the surface of roughened 31×23 cm polypropylene surface containing dried analyte using a 7 cm diameter polypropylene funnel installed 3 cm above the surface. The funnel was connected by flexible tubing to a polypropylene impinger containing 30 mL of water. The outlet of the impinger was connected to a suction pump set at a 5 L/min rate. Collection of airborne particles was performed over 24 hr and a sample of the solution was submitted for PCR analysis. Untreated surface amplicon produced PCR signal at Ct 35. The surface that was treated by spraying of 0.1% Compound 1 solution and then dried overnight showed no detected amplicon (FIG. 4). Similarly, solutions of Compound 1 in 0.01% showed complete suppression of amplicon and partial suppression using 0.001% COMPOUND 1 (Table 2). In all cases, 10K copies of the target DNA added to PCR samples showed the same Ct as a control, demonstrating that no PCR inhibitor was generated in aerosol state.

To demonstrate that no PCR inhibitor was generated in aerosolized form, 1% Compound 1 was applied to the clean roughened polypropylene surface and dried overnight. Aerosol was trapped with 30 mL water over 24 hr, and a sample was tested by PCR with added 10K target DNA. The PCR didn't show difference in Ct compared to the control sample of 10K target DNA in pure water (Table 2).

TABLE 2

Inactivation of amplicon in aerosolized form sprayed by solutions of Compound 1

| Sample | Ct | Ct with added 10K DNA |
|---|---|---|
| No treatment control | 36 | 13 |
| 0.1% Compound 1 | ND | 14 |
| 0.1% Compound 1 | ND | 17 |
| 0.01% Compound 1 | ND | ND |
| 0.001% Compound 1 | 46 | 16 |
| 1% Compound 1; no amplicon 24 hr | ND | 16 |
| 1% Compound 1; no amplicon 72 hr | ND | 16 |

Example 5 Scrubber for Decontaminating Air from Amplicon

Aerosol was collected above the surface of roughened 31×23 cm polypropylene surface containing dried amplicon using a 7 cm diameter polypropylene funnel installed 3 cm above the surface. The funnel was connected by flexible tubing to a polypropylene impinger A containing 30 mL of water. Another impinger B with 30 mL of water was connected in series with impinger A. The outlet of the impinger B was connected to a suction pump set at a 5 L/min rate. Collection of airborne particles in impinger A and then subsequently in impinger B was performed over 24 hr and samples of the solutions from A and B were submitted to PCR analysis. Aerosol from surface amplicon produced PCR signal at Ct 35 from A and 42 from B. This experiment demonstrates that water was not effective scrubbing substance: amplicon still escape from impinger A resulting in detection of amplicon in impinger B.

Another similar experiment was performed with two impingers A and B connected in series, except A was filled with 30 mL of 0.1% Compound 1. PCR analysis demonstrated no active amplicons (ND) in either impinger, while sample from B also demonstrated no PCR inhibition.

TABLE 3

Air purification from amplicon by using scrubber containing Compound 1

| Setup | Impinger A | A + 10K DNA | Impinger B | B + 10K DNA |
|---|---|---|---|---|
| Water in A and B | 35 | 19 | 42 | 19 |
| 0.1% Compound 1 in A and water in B | ND | 17 | ND | 16 |

What is claimed is:

1. A method of reducing nucleic acid contamination on a surface comprising: contacting a surface contaminated with a nucleic acid with a composition comprising an amidated pectin comprising one or more monomeric units represented by

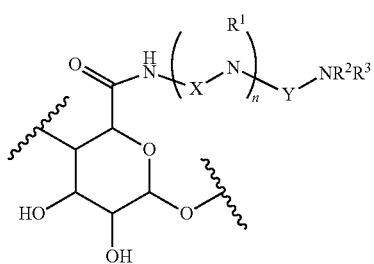

or a tautomer, an isomer, or a salt thereof, wherein:
n is 0, 1, 2, or 3;
$R^1$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^2$ and $R^3$ are independently H or $C_1$-$C_3$ alkyl.

2. The method of claim 1, wherein the molecular weight of the amidated pectin is between about 0.5 kDa and about 500 kDa.

3. The method of claim 1, wherein the composition comprising the amidated pectin is a solution of the amidated pectin.

4. The method of claim 3, wherein the amidated pectin is in solution at a concentration of about 0.01% to about 5%.

5. The method of claim 3, wherein the amidated pectin in solution with a concentration of from about 1 ug/mL to about 1000 ug/mL.

6. A method for reducing nucleic acid contamination in a solution, comprising: contacting a solution contaminated with a nucleic acid with a solid support comprising an amidated pectin covalently bound thereto, wherein the amidated pectin comprises one or more monomeric units represented by or a tautomer, an isomer, or a salt thereof, wherein:
n is 0, 1, 2, or 3;
$R^1$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^2$ and $R^3$ are independently H or $C_1$-$C_3$ alkyl.

7. The method of claim 6, wherein the solid support is a magnetic bead, glass bead, polystyrene bead, polystyrene filter, or glass filter.

8. A method of reducing aerosolized nucleic acid contamination in air, comprising contacting air contaminated with aerosolized nucleic acid with a composition comprising an amidated pectin comprising one or more monomeric units represented by or a tautomer, an isomer, or a salt thereof, wherein:
n is 0, 1, 2, or 3;
$R^1$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^2$ and $R^3$ are independently H or $C_1$-$C_3$ alkyl.

9. The method of claim 8, wherein contacting the air contaminated with aerosolized nucleic acid comprises passing the air through a filter comprising the amidated pectin.

10. The method of claim 8, wherein contacting the air contaminated with aerosolized nucleic acid comprises passing the air above a surface comprising the amidated pectin covalently bound thereto.

11. The method of claim 1, wherein the amidated pectin comprises one or more monomeric units represented by:

or an isomer, a salt, or a tautomer thereof.

12. The method of claim 6, wherein the amidated pectin comprises one or more monomeric units represented by:

or an isomer, a salt, or a tautomer thereof.

13. The method of claim 8, wherein amidated pectin comprises one or more monomeric units represented by:

-continued
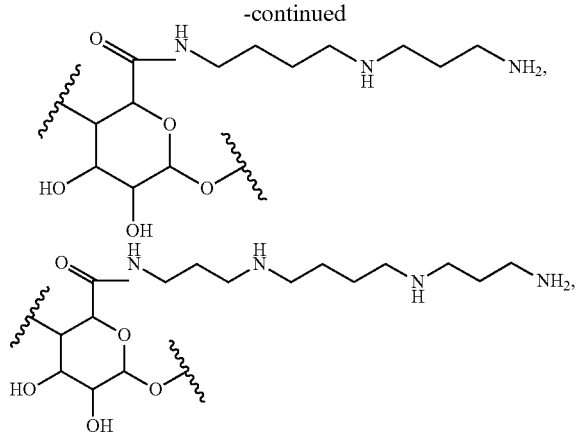
or an isomer, a salt, or a tautomer thereof.
* * * * *